Figure 1:
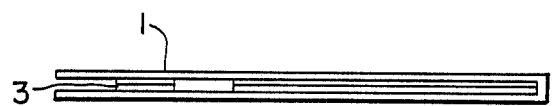

United States Patent [19]

Sato et al.

[11] Patent Number: 4,806,380

[45] Date of Patent: Feb. 21, 1989

[54] FINGERPRINT DEVELOPER

[75] Inventors: Mitsuyoshi Sato; Akihiko Hiraiwa; Kaoru Kimura, all of Nagoya, Japan

[73] Assignee: Toagosei Chemical Industry, Co., Tokyo, Japan

[21] Appl. No.: 147,083

[22] Filed: Jan. 20, 1988

Related U.S. Application Data

[63] Continuation of Ser. No. 886,669, Jul. 16, 1986, abandoned.

[30] Foreign Application Priority Data

Aug. 28, 1985 [JP] Japan .................................. 60-187321

[51] Int. Cl.$^4$ ............................ A61B 5/10; B41K 1/00
[52] U.S. Cl. ....................................... 427/1; 118/31.5; 427/145; 428/419; 428/516; 428/34.2
[58] Field of Search ................... 118/31.5; 427/1, 145; 428/35, 419, 516

[56] References Cited

U.S. PATENT DOCUMENTS

| | | | |
|---|---|---|---|
| 4,407,842 | 10/1983 | Shepard | 427/1 |
| 4,461,235 | 7/1984 | Morton | 427/1 |
| 4,504,408 | 3/1985 | Morton | 118/31.5 |
| 4,550,041 | 10/1985 | Thompson et al. | 427/1 |

*Primary Examiner*—Janyce Bell
*Attorney, Agent, or Firm*—Wyatt, Gerber, Burke and Badie

[57] ABSTRACT

Fingerprint developers are made of woven or non-woven fabric of hydrophobic synthetic fibers which is impregnated with 2-cyanoacrylate. The synthetic resin for the fibers may be polyethylene, polypropylene and the like. This developer is placed in a closed vessel together with an article suspected of containing a latent fingerprint with or without a cup of hot water. Rapid development of fingerprints is possible.

8 Claims, 1 Drawing Sheet

FINGERPRINT DEVELOPER

This is a continuation of application Ser. No. 886,669 filed July 16, 1986, now abandoned.

The present invention relates to a fingerprint developer, particularly a fingerprint developer system which can expose latent fingerprints attached to surfaces of various articles.

Fingerprint developers are now familiar in criminal investigation for services such as identification.

It is well known to develop latent fingerprints using the white residue formed when 2-cyanoacrylate is polymerized and cured. This was first put to practical use in the Japanese National Police Agency and there are many reports thereon in Identification News, U.S.A., and other publications. For instance, U.S. Pat. No. 4,297,383 discloses a method in which an article suspected of containing a latent fingerprint is subjected in one chamber to 2-cyanoacrylate vapors generated from another chamber to develop the fingerprint. Various kits for the development of fingerprints are commercially available in U.S.A., for example, "Dura-Print kit" (trade name) manufactured by San Francisco Company, "Super-Fume" (trade name) by U.S. Lightning Powder Co. and "Super-Glue Fuming Kit" (trade name) by Fairchild Lowell Co. The "Dura-Print Kit" mentioned above, for example, uses cotton treated with sodium hydroxide in order to accelerate the generation of vapors, and 2-cyanoacrylate is dropped thereon to vaporize the 2-cyanoacrylate. U.S. Pat. No. 4,477,607 discloses a thixotropic cyanoacrylate-containing composition for fingerprint development, and "Hard Evidence" (trade name) manufactured by Loctite Co., which is available in the market which appears to be based thereon.

One of problems is that the generation rate of monomer vapor is low, when 2-cyanoacrylate is used for development of latent fingerprints. In order to deal with the problem, there various proposals, e.g., the use of heat or the use of cotton treated with sodium hydroxide mentioned above. However, none of them is completely satisfactory. In the latter method, polymerization and curing take place at a more rapid rate than generation of monomer vapor and an amount of the vapor generated is undesirably low. Furthermore, the method requires handling of sodium hydroxide. In the former method, dection of fingerprints is often difficult owing to overdevelopment. Furthermore, it is very hard to control temperature in a heating processes. In addition, articles suspected of containing latent fingerprints are often damaged by heat, particularly when the articles are made of plastics. Another approach to accelerate the generation of vapors is impregnation of 2-cyanoacrylate into filter papers or blotter. However, this approach is not satisfactory yet, because a large amount of 2-cyanoacrylate to impregnate substrate and polymerization often occurs on the surface of the substrate Another problem encountered when 2-cyanoacrylate is used for development of latent fingerprints is that the compositions drip. This problem is avoided by using highly thixotropic cyanoacrylate that is substantially non-flowable. However, this procedure is not satisfactory, because it takes a long time for preparation of the compositions. Furthermore, more time is necessary for development, because the low generation rate of monomer vapors becomes more and more critical.

The present invention improves the rate of vapor generation and shortens the period of time required for development of latent fingerprints. The present invention, too, overcomes difficulties in handling owing to dripping.

It has been found that the use of woven or nonwoven fabric made of synthetic resin and impregnated with a selected 2-cyanoacrylate assists in avoiding the problems mentioned above. According to the present invention, the developer product comprises woven or nonwoven fabric made of synthetic resin impregnated with 2-cyanoacrylate. It is capable of generating a large amount of vapor of 2-cyanoacrylate monomer. The developer may be hung from or fixed to a ceiling, because no dripping is observed. Furthermore, the present developer is superior in storage stability. It is possible to package and transport the present developer in suitable materials, e.g., metal foil without significant loss of effectiveness.

2-cyanoacrylate

Preferred 2-cyanoacrylates for the present invention have high vapor pressure and ready to produce a white residue when polymerization and curing. Those include, for example, methyl 2-cyanoacrylate and ethyl 2-cyanoacrylate. Alternatively, the following may be employed alone or in the form of mixture, with or without the above methyl 2-cyanoacrylate and/or ethyl 2-cyanoacrylate: n-propyl 2-cyanoacrylate, isopropyl 2-cyanoacrylate, n-butyl 2-cyanoacrylate, isobutyl 2-cyanoacrylate, allyl 2-cyanoacrylate and propargyl 2-cyanoacrylate.

Cyanoacrylate adhesives presently available in the market may be employed, because the adhesives contain a substantial amount of 2-cyanoacrylate monomer. However, a large amount of stabilizers are needed in the case where the commercial adhesives are employed, because such adhesives do not generate significant amount of monomer vapor and are not stable in storage. This problem to may be avoided by the use of stabilizers, for example, sulfur dioxide, sulfonic acids, sultone, boron fluoride, acetic acid, trifluoroacetic acid, phosphoric acid, hydroquinone, catechol and pyrogallol. Any amount of the stabilizer may be used so long as the development of fingerprints is not damaged. Such 2-cyanoacrylate products are not useful as adhesives.

The 2-cyanoacrylate compositions used in the invention may be of low viscosity, but should be sufficiently viscous so that generation of monomer vapor is not harmed dripping is controlled. The preferred viscosity is 2–100,000 cps, more preferably 2–10,000 cps. Too high a viscosity renders vapor pressure too low, and impedes impregnation amount into woven or nonwoven fabric. Thickeners, for example synthetic resins such as methyl methacrylate polymer, acrylic rubber and cellulose ester or fumed silica may be employed to increase viscosity.

Woven or nonwoven fabric

The fabric used in the invention is made of synthetic fibers. Fabric made of natural or inorganic fibers is not usable in this invention, since 2-cyanoacrylate is liable to polymerize because of the moisture on the surface of the fibers. As a result there is insufficient generation of monomer vapor a low storage stability.

The synthetic resin for the fibers of the invention is hydrophobic and is insoluble in 2-cyanoacrylate. If the synthetic resin is soluble or swells in 2-cyanoacrylate, the fabric will lose its woven or nonwoven structure after impregnation with the 2-cyanoacrylate. If the synthetic resin is hydrophilic, performance of the fabric will not be acceptable, since water is often adsorbed on the surfaces of fibers, and this causes polymerization. Synthetic resins useful in the practice of the invention include, for example, polyethylene, polypropylene, polyester and polyethylene tetrafluoride.

The form of the present fabric may be that for usual cloths, backing for cloths or materials for industrial uses, for example, oil-absorbing materials for a filter. Typically useful fibers include "Teijin Unisel" IP 100K (trade mark) manufactured by Teijin Limited, Japan and made from polyester, and "Teijin Olsorb" (trade mark) manufactured by Teijin Limited, Japan and made from polypropylene.

Development of fingerprints

The present developer is usable in the conventional method effected in a closed vessel. For instance, an article suspected of containing a latent fingerprint is left to stand in a closed vessel in which there are the present developer, i.e., a piece of woven or nonwoven fabric of synthetic resin impregnated with 2-cyanoacrylate and, if necessary, a cup of hot water. Monomer vapor generates and polymerizes at the latent fingerprint to expose the fingerprint with the white residue. The hot water is not always necessary. Hot water provides moisture which accelerates formation of white residue. The Period of time required for development varies depending on the volume of a vessel, area of a piece of woven or nonwoven fabric and the amount of 2-cyanoacrylate impregnated. Usually it is from a few minutes to a few hours.

The present development system is, typically, employed in a room or an automobile the area of the fabric and the amount of 2-cyanoacrylate impregnated should be controlled relative to the internal volume of the room or automobile.

The present fingerprint developer should be stored or transported in a sealed container. One useful container is an envelope made of, for example, gas-impermeable plastic film, metal foil, or a piled sheet thereof. A number of useful products are available commercially.

Figure 2:
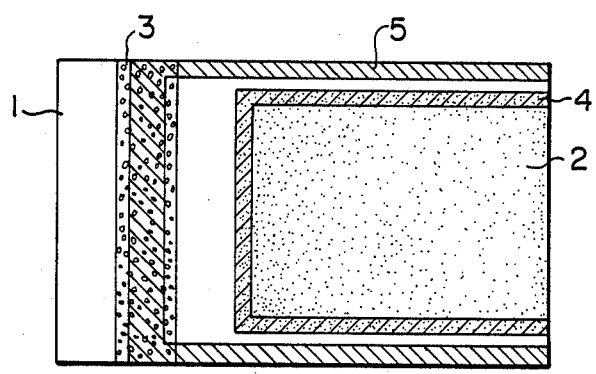
Figure 3:
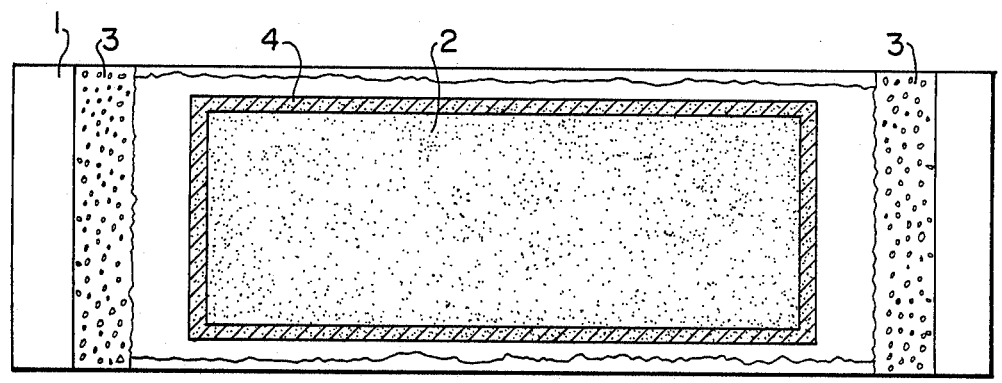

A sample of a commercial package is shown in the accompanying drawings. FIG. 1 is a sectional view, FIG. 2 a front perspective view and FIG. 3 a front view when opened.

In the drawings, 1 is package paper made from film of polyethylene (PE) (inside)/Al/PE/craft paper (outside), 2 is a nonwoven fabric of "Teijin Unisel" BT 0908 W (trade mark) in which 2-cyanoacrylate is impregnated, 3 is a sealant, 4 is a fixed part of the nonwoven fabric and 5 is a heatsealed part of the package paper, and 3, 4 and 5 are heatsealed together.

The present improvement in the of generation of monomer vapor appears to relate to the fact that the surface area of fibers for woven or nonwoven fabric is very large. Suprisingly, no increase of viscosity or curing in 2-cyanoacrylate is observed in the present invention, although 2-cyanoacrylate applied thinly on a surface of an article usually polymerizes in a short time to cause such change. The amount of vapor of 2-cyanoacrylate is as high as at least 50% even after four hours under 60% RH at 23° C.

The oil-absorbing property of the woven or nonwoven fabric apparently controls dripping of 2-cyanoacrylate.

Stability in storage is improved by the addition of stabilizers to 2-cyanoacrylate. The superiority of the present developer in storage stability is apparently due to to the fact that the present fabric which is impregnated with 2-cyanoacrylate is made of a hydrophobic synthetic resin which absorbs only a small amount of water. There is very little polymerization despite the fact that the 2-cyanoacrylate is thinly applied onto the surface of fibers of the woven or nonwoven fabric.

The present invention will be better understood by reference to be following non limiting examples and comparison examples.

EXAMPLES 1–7

Several pieces (5 cm×5 cm) of nonwoven fabric made of "Teijin Unisel" IP 100 K (trade mark) were uniformly impregnated with 2-cyanoacrylate (1 g each) containing additives shown in Table 1.

Vaporization speed test

Pieces of the nonwoven fabric above were horizontally laid on polyethylene plates and placed in a room (23° C., 60% RH). The amounts of monomer vaporized were calculated on the basis of weight difference after four hours.

Dripping test

Similar pieces of fabric to the above were hung vertically for 24 hours in a room (23° C., 60% RH), to observe how much 2-cyanoacrylate dripped.

Stability test

Similar pieces of fabric to the above were place in a bag made of aluminium (20 μm)/polyethylene (10 μm) laminated film and heated at 60° C. for 10 days.

Development test of fingerprints

Nonwoven fabrics impregnated with 2-cyanoacrylates of examples 1–7, respectively, a beaker (50 ml each) containing hot water at about 50° C. and a chloroprene sheet containing latent fingerprints were placed in polyethylene vessels with covers (4 l each). The vessel each was placed in a room (23° C., 60% RH). Clearness of white residue was observed after 15 min.

Results are shown in Table 3.

Comparison examples 1 and 2

2-cyanoacrylate (1 g each) containing respective additives shown in Table 2 was applied (5 cm×5 cm) uniformly on polyethylene plates.

Amounts of monomer vaporized were observed as in Examples 1–7.

Development test as in Examples 1–7 was repeated except that polyethylene plates on which the same 2-cyanoacrylates as above were applied, respectively, were employed in place of the nonwoven fabric.

Results are shown in Table 3.

Comparison examples 3–4

Cotton which was thoroughly impregnated with aqueous 0.5N sodium hydroxide solution, dried and cut into pieces (5 cm×5 cm).

Development test as in Examples 1–7 was repeated except that the cotton pieces were employed in place of the nonwoven fabric. 2-cyanoacrylates (3 g each) as shown in Table 2 were uniformly sprinkled thereon just before the cover was put on the vessel.

No development of latent fingerprints was observed even after 15 min., although fumes were generated after about 40 and 90 seconds.

These examples substantiate the fact that clear development with high certainty of latent fingerprints is possible in a short time. This greatly facilitates the observation of fingerprints which is useful in criminal investigation.

TABLE 1

| Example | Monomer (viscosity) | Additives and amount thereof | |
|---|---|---|---|
| Example 1 | Methyl 2-cyanoacrylate (2 cps) | SO$_2$<br>p-Toluenesulfonic acid<br>Hydroquinone | 20 ppm<br>2000 ppm<br>2000 ppm |
| Example 2 | Methyl 2-cyanoacrylate (100 cps) | Polymethyl methacrylate<br>SO$_2$<br>p-Toluenesulfonic acid<br>Hydroquinone | 3%<br>20 ppm<br>2000 ppm<br>2000 ppm |
| Example 3 | Methyl 2-cyanoacrylate (1500 cps) | Polymethyl methacrylate<br>Methanesulfonic acid<br>Hydroquinone | 6%<br>2000 ppm<br>2500 ppm |
| Example 4 | Ethyl 2-cyanoacrylate (2 cps) | SO$_2$<br>p-Toluenesulfonic acid<br>Hydroquinone | 200 ppm<br>2000 ppm<br>2000 ppm |
| Example 5 | Ethyl 2-cyanoacrylate (100 cps) | Polymethyl methacrylate<br>SO$_2$<br>p-Toluenesulfonic acid<br>Hydroquinone | 3%<br>20 ppm<br>2000 ppm<br>2000 ppm |
| Example 6 | Ethyl 2-cyanoacrylate (100 cps) | Polymethyl methacrylate<br>SO$_2$<br>Phosphoric acid<br>Hydroquinone | 3%<br>20 ppm<br>2000 ppm<br>2000 ppm |
| Example 7 | Isopropyl 2-cyanoacrylate (200 cps) | Cellulose acetate butylate<br>SO$_2$<br>p-Toluenesulfonic acid<br>Hydroquinone | 3%<br>20 ppm<br>2000 ppm<br>2000 ppm |

TABLE 2

| | Monomer | Additives and amount thereof | |
|---|---|---|---|
| Comparison Example 1* | Methyl 2-cyanoacrylate | Polymethyl methacrylate<br>Methanesulfonic acid<br>Hydroquinone<br>CAB-O-SIL N70-TS | 6%<br>2000 ppm<br>2500 ppm<br>6% |
| Comparison Example 2 | Ethyl 2-cyanoacrylate | Polymethyl methacrylate<br>SO$_2$<br>p-Toluenesulfonic acid<br>Hydroquinone | 3%<br>20 ppm<br>2000 ppm<br>2000 ppm |
| Comparison Example 3 | Ethyl 2-cyanoacrylate | SO$_2$<br>Hydroquinone | 20 ppm<br>200 ppm |
| Comparison Example 4 | Ethyl 2-cyanoacrylate | SO$_2$<br>p-Toluenesulfonic acid<br>Hydroquinone | 20 ppm<br>2000 ppm<br>2000 ppm |

*320,000 cps on B type viscometer with Helicalstand and TE spindle at 2.5 rpm (25 ± 1° C.)

TABLE 3

| | Vaporization of monomer (%) | Dripping | Stability | Clearness of fingerprints* |
|---|---|---|---|---|
| Example 1 | 70 | None | Good | |
| Example 2 | 68 | None | Good | |
| Example 3 | 60 | None | Good | |
| Example 4 | 60 | None | Good | |
| Example 5 | 54 | None | Good | |
| Example 6 | 58 | None | Good | |
| Example 7 | 52 | None | Good | Δ |
| Comparison Example 1 | 45 | — | — | Δ |
| Comparison Example 2 | 40 | — | — | Δ |
| Comparison Example 3 | — | — | — | × |
| Comparison Example 4 | — | — | — | × |

*Notes
Very good
Δ Good
× No good

EXAMPLE 8

Example 1 was repeated except nonwoven fabric made of polypropylene fibers "Teijin Olsorb" (trade mark) was used in place of the "Teijin Unisel" IP 100K. The result was the same as of Example 1 except vaporization of monomer was 67% instead of 70%.

What is claimed is:

1. A fingerprint developer system which comprises woven or nonwoven fabric of hydrophobic synthetic fibers impregnated with a composition, the major proportion of which is a 2-cyanoacrylate, said fibers being substantially insoluble in the 2-cyanoacrylate.

2. A fingerprint developer system according to claim 1 wherein the fibers are polyethylene fibers, polypropylene fibers, polyester fibers or polyethylene tetrafluoride fibers.

3. A fingerprint developer system according to claim 1 wherein the 2-cyanoacrylate has viscosity of 2–100,000 cps.

4. A fingerprint developer system according to claim 1 wherein the 2-cyanoacrylate is methyl 2-cyanoacrylate or ethyl 2-cyanoacrylate.

5. A fingerprint developer system according to claim 1 wherein the 2-cyanoacrylate is selected from the group consisting of n-propyl 2-cyanoacrylate, isopropyl 2-cyanoacrylate, n-butyl 2-cyanoacrylate, isobutyl 2-cyanoacrylate, allyl 2-cyanoacrylate and propagyl 2-cyanoacrylate.

6. A fingerprint developer system according to claim 6 wherein the 2-cyanoacrylate is used together with methyl 2-cyanoacrylate or ethyl 2-cyanoacrylate.

7. A fingerprint developer system according to claim 1 wherein the 2-cyanoacrylate contains a stabilizer selected from the group consisting of sulfur dioxide, a sulfonic acid, sultone, boron fluoride, acetic acid, trifluoroacetic acid, phosphoric acid, hydroquinone, catechol and pyrogallol.

8. A fingerprint development package comprising woven or nonwoven fabric of hydrophobic synthetic fibers impregnated with a composition, the major proportion of which is a 2-cyanoacrylate in a sealed package, said fibers being substantially insoluble in the 2-cyanoacrylate.

* * * * *